(12) United States Patent
Albright

(10) Patent No.: US 6,348,629 B1
(45) Date of Patent: Feb. 19, 2002

(54) FREE RADICAL INHIBITORS FOR QUENCHING AQUEOUS PHASE POLYMER GROWTH AND RELATED METHODS

(75) Inventor: Robert Albright, Churchville, PA (US)

(73) Assignee: Sun Drilling Products Corp., Belle Chasse, LA (US)

( * ) Notice: Subject to any disclaimer, the term of this patent is extended or adjusted under 35 U.S.C. 154(b) by 0 days.

(21) Appl. No.: 09/925,432

(22) Filed: Aug. 9, 2001

Related U.S. Application Data

(63) Continuation of application No. 09/138,839, filed on Aug. 24, 1998, now abandoned.

(51) Int. Cl.$^7$ .......................... C07C 239/08; C08F 2/38
(52) U.S. Cl. .......................... 564/301; 564/84; 564/86; 564/113; 564/199; 564/204; 564/503; 564/506; 536/51; 536/112; 548/544; 568/704; 568/949; 526/83; 526/199; 526/200; 252/401; 252/403
(58) Field of Search .......................... 526/83, 199, 200; 564/84, 86, 113, 199, 204, 301, 503, 506; 536/51, 112; 548/544; 568/704, 949; 252/401, 403

(56) References Cited

U.S. PATENT DOCUMENTS

| | | | |
|---|---|---|---|
| 4,104,196 A | 8/1978 | Zaffaroni | 252/404 |
| 5,998,555 A | 12/1999 | Vijayaraghavan et al. | 526/204 |

OTHER PUBLICATIONS

W. P. Hohenstein and H. Mark, "Polymerizations in Suspension and Emulsion" pp, 1–74, in *High Molecular Weight Organic Compounds*, (Dover Publications) Interscience Publishers, Inc. New York, 1949.
Edited by R. E Burk and O. Grummitt; Vol. VI of *Frontiers in Chemistry*.

J.V. Minkiewicz, D. Milstein, J. Lieto, B.C. Gates, and R.L. Albright, "Preparation and Characterization of Poly(styrene–divinylbenzene)–Supported Catalysts", pp. 9–30, in *Chemically Modified Surfaces in Catalysis and Electrocatalysis*, Edited by J.S. Miller, ACS Symposium Series 192, American Chemicaly society, Washington, D.C., 1982.

D.C. Sherrington, "Preparation, Functionalization and Characteristics of Polymer Supports", pp. 1–82, in *Polymer–Supported Reactions in Organic Synthesis*, Edited by P. Hodge and D.C. Sherrington, John Wiley & Sons, Inc., New York, 1980; also, Appendix, pp. 469–478, in Polymer–supported Reactions in Organic Synthesis.

F.H. Winslow and W. Matreyek, Ind. Eng. Chem. 43, pp. 1108 (1951).

A.K. Sengupta, "Chromate Ion Exchange", pp. 115–148, in *Ion Exchange Technology: Advances in Pollution Control*, Edited by A.K. Sengupta, Technomic Publishing Co., Inc., Lancaster, PA. USA, 1995.

J. Applied Polymer Science, 27, 133–138 (1982); "Particle Size Control in Suspension Copolymerization of Styrene, Chloromethystyrene, and Divinylbenzene;" T, Balakrishnan and W.T. Ford.

M. Tanka and K. Hosogai, J. Applied Polymer Science, 39, 955–966 (1990); Suspension "Polymerization of Styrene with Circular Loop Reactor."

*Primary Examiner*—Fred Teskin
(74) *Attorney, Agent, or Firm*—Morgan, Lewis & Bockius LLP

(57) ABSTRACT

An aqueous phase inhibitor for quenching free radical polymerization comprising a free radical quenching agent having a hydrophilic tail is disclosed, as well as a coating and related methods. In one embodiment, the free radical quenching agent can either be an N-hydroxylamine or an N-nitrosonamine, the hydrophilic tail can be a polyhydric alcohol tail and the inhibitor can be a concentrate in a liquid medium such as water, alcohol and mixture thereof.

16 Claims, No Drawings

FREE RADICAL INHIBITORS FOR QUENCHING AQUEOUS PHASE POLYMER GROWTH AND RELATED METHODS

This application is a continuation of U.S. patent application Ser. No. 09/138,839, entitled "FREE RADICAL INHIBITORS FOR QUENCHING AQUEOUS PHASE POLYMER GROWTH AND RELATED METHODS" field on Aug. 24, 1998 in the name of Robert Albright now abandoned.

FIELD OF INVENTION

The present invention relates to an aqueous phase inhibitor for quenching free radical polymerization in the aqueous phase and related methods. The invention also relates to a coating for providing protection against polymer growth on walls of polymerization vessels and associated equipment including reactors, and on baffles, blades and shafts of agitators.

BACKGROUND OF INVENTION

Most crosslinked polymers and linear polymers are manufactured by free-radical-initiated chain polymerization. Free radical polymerization is the linking together of monomer units under the influence of a free radical initiator. A free radical initiator is a reactive molecular fragment with an unpaired electron. Such polymerization when carried out in an immiscible liquid is also known as suspension polymerization, pearl polymerization, droplet polymerization, and dispersion polymerization The polymerization are usually performed with water as the immiscible liquid. The polymeric product is made handleable and manageable by this technique, since the polymer is broken-up into spherical droplets before it is formed. In such a polymerization, the monomer mixture containing an initiator is suspended in an immiscible liquid as droplets. The liquid most used for making a slurry of monomer droplets is water. Water is preferred for dispensing liquid since most organic monomers have a very small solubility in water or, if the monomer is water soluble, can usually be salted out by the addition of an electrolyte. The monomer droplets are converted into beads of polymer by heating the slurry to a temperature where the dissolved initiator thermally decomposes into free radicals at a sensible rate. A sensible rate is achieved at a temperature where the half-life of the dissolved initiator is between from about five to about ten hours. This temperature is maintained until the monomer droplets are transformed into beads of solid polymer with essentially no remaining monomer. A higher temperature step then may be applied to the bead slurry in order to destroy the remaining unreacted initiator.

Since all organic monomers have a small but finite solubility in water, monomer diffuses from the droplets into the water phase. If this molecularly dispersed monomer dissolved in the water phase is not protected against polymer growth, it will polymerize during the process in the water phase by initiation from free radicals that arrive in the water phase from the droplets of monomer or by thermal initiation of the monomer itself. Such polymers are much smaller in size (0.005 to 1.0 micron in diameter) than that being formed in droplets (30 to 3000 microns in diameter), and, therefore, produces a milky white aqueous liquor. This polymer, which is called an emulsion polymer, is an unwanted byproduct of the droplet polymerization process, and converts valuable monomer into waste polymer.

SUMMARY OF THE INVENTION

The present invention relates to an aqueous phase inhibitor for quenching free radical polymerization in the aqueous phase. For purposes of this invention the term "inhibitor" refers to a molecule that terminates the growth of free radical polymerization by interacting with the radical terminus of the polymer chain so as to remove its energy for continued reaction with monomer, and the term "quench" means to suppress, to stop or to destroy. The inhibitor comprises a free radical quenching agent or moiety having a hydrophilic tail. The term "hydrophilic tail" refers to a molecular fragment that is solvated by water. The hydrophilic tail can be a polyhydric alcohol. The polyhydric alcohol tail can comprise from about three to about one thousand carbon atoms, each of the carbon atoms being attached to hydroxyl group except for the carbon atom attached to the N-hydroxylamine. The hydrophilic tail can also be selected from sugar molecules, dextrans, inositol, sorbitol, polyvinylalcohols, polyethylene oxides, aminoacids, oligomers of N-vinylpyrrolidinone, oligomers of N-vinyl formamide, oligomers of acrylamide, oligomers of methacrylamide, p-benzamide, p-benzenesulfonamide, etc.

In one embodiment of the invention, the free radical agent or moiety is N-hydroxylamines. In another embodiment, the free radical agent or moiety is N-nitrosonamine.

The inhibitor of the present invention can be applied as a concentrate in a liquid medium such as water, alcohol and mixture thereof.

In another embodiment, the aqueous phase inhibitor can be N-hydroxyl-N-methylglucamine and the liquid medium is water. The N-hydroxyl-N-methylglucamine can be from about 15 to about 40% of the solution. In a further embodiment, the aqueous phase inhibitor can be N-nitrous-N-methylglucamine and the liquid medium is water. The N-nitrous-N-methylglucamine can be from about 15 to about 40% of the solution.

Unlike other inhibitors whose hydrophilicity is provided by ion formation, the hydrophilicity of the inhibitors of the present invention is provided by a non-ionic carbon chain carrying polarizable groups that are solvated by water through dipole-dipole interaction and by hydrogen bonding. Consequently, the inhibitors of this invention retain their water solubility throughout the entire aqueous pH range. In suspension polymerization, pH control over the aqueous phase is unnecessary. The hydrophilic tail also makes these inhibitor molecules immiscible within the hydrophobic monomer droplets, and this immiscibility precludes quenching the desired polymer development within the droplets.

In yet another embodiment, the present invention also provides a coating for protection against polymer growth. For purposes of this invention, the term "coating" refers to a covering by filming over the surface of the material so as to change the nature of the surface. Most coatings have polar oxide surface layers that will bind to molecules that are dipoles. The coating comprises a free radical quenching agent having a hydrophilic tail. Since these inhibitor molecules have a hydrophilic tail of multi-carbon chains with polarizable groups, they have interfacial activity and seek the interface between the liquid phase and the solid surfaces of reaction vessels and associated equipment such as reactors and agitators. The hydrophilic tail of the quenching agent have dipole oxygen groups for which the oxides surface of the metals has a propensity to bind and form dipole-dipole interactions. By filming out on the reactor surfaces, they act as polymer growth inhibitors or as a coating on the reactor walls, and baffles, stirring blades, and shafts of agitators. The coating on the surfaces of the reactors and agitators keeps the reactors and agitators clean and operable for long periods of times. The metal of reactor, particularly stainless steel reactor, can act as a template for polymer film growth. For example, as many as 100 batches of beads were manufactured in between kettle cleanings in the suspension polymerization of styrene-divinyl-benzene monomer with the use of the inhibitor, N-hydroxy-N-methylglucamine, at the level of 0.03 to 0.5 wt. % of the aqueous phase. A typical manufacturing cycle between kettle cleanings is five to seven batches with the styrene-divinyl-benzene monomer system.

The free radical quenching agent or moiety of the present invention can be N-nitrosoamines and N-hydroxylamines. The hydrophilic tail can be polyhydric tail and the polyhydric tail can comprises from about three carbon atoms to about one thousand carbon atoms, each of the carbon atoms can be attached to a hydroxyl group except the carbon atom attached to the nitrogen of the group. The hydrophilic tails can also constructed from sugar molecules, dextrans, mositol, sorbitol, poly(vinyl-alcohol)s, poly(ethylene oxide)s, aminoacids, oligomers of N-vinylpyrrolidinone, oligomers of N-vinylformamide, oligomers of acrylamide, oligomers of methacrylamide, p-benzamide, p-benzene sulfonamide, etc.

In a further embodiment, the present invention also relates to a method for quenching of radical polymerization in the aqueous phase. The method comprises the step of providing a free radical quenching agent or moiety having a hydrophilic tail. The agent can be N-hydroxylamine or N-nitrosoamine. The hydrophilic tail can be a polyhydric alcohol tail. The polyhydric alcohol tail can comprise from about three carbon atoms to about one thousand carbon atoms, each of the carbon atoms being attached to a hydroxyl group except the carbon atom attached to the nitrogen of the N-hydroxylamine or the N-mitrosoamine. The hydrophilic tail can also be selected from sugar molecules, dextrans, inositol, sorbitol, polyvinylalcohols, polyethylene oxides, amino acids, oligomers of N-vinylpyrrolidinone, oligomers of N-vinylformamide, oligomers of acrylamide, oligomers of methacrylamide, p-benzamide and p-benzenesulfonamide.

In one embodiment, the inhibitors is N-hydroxyl-N-methyglylamine and in another embodiment, the inhibitor is N-nitroso-N-methylglucamine. In a further embodiment, the method further comprises the step of dissolving the agent in a liquid medium such as water, alcohol and mixtures thereof.

In still another embodiment, the present invention also relates to a method for coating a surface against polymer growth. The method comprises the step of applying a free radical quenching agent or moiety having a hydrophilic tail to a surface. The surface can be the walls of a reactor and the baffles, blades, and shaft of the agitator. The agent or moiety can be N-hydroxylamine or N-nitrosoamine. The polyhydric alcohol tail comprises from about three carbon atoms to about one thousand carbon atoms, each of the carbon atoms being attached to a hydroxyl group except the carbon atom attached the nitrogen of the N-hydroxylamine or the N-nitrosoanime. The hydrophilic tail consisting essentially of sugar molecules, dextrans, mositol, sorbitol, polyvinylalcohols, polyethylene oxides, amino acids, oligomers of N-vinylpyrrolidinone, oligomers of N-vinylformamide, oligomers of acrylamide, oligomers of methacrylamide, p-benzamide and p-benzenesulfonamide. In one embodiment, the method further comprises the step of dissolving the agent in a liquid medium before applying the agent to the surface. The liquid medium consist essentially of water, alcohol and mixtures thereof. the agent can be applied to the surface by spraying, brushing and other numerous application methods.

DETAILED DESCRIPTION OF THE INVENTION

The inhibitor of the present invention exhibits many advantageous properties including the following properties: is immiscible or insoluble within the droplets of monomer; is miscible or soluble in the aqueous phase; is effective at quenching free radicals that arise in the aqueous phase; remains in the aqueous phase throughout the transformation of the monomer droplets into polymeric particles; and the quenching lifetime for the inhibitor lasts essentially throughout the time needed to polymerize the monomer droplets.

The following examples which describe the method of synthesis of aqueous phase free radical quenching agents for use in suspension polymerization are illustrative of the invention in more detail and are not intended to be construed in anyway as limitations to the invention.

EXAMPLE 1

Synthesis of a 30% Aqueous Solution of N-Hydroxy-N-Methylglucamine

This reaction was exothermic and the temperature must be kept below 55° C. in order that the molecule did not begin to self-destruct.

395.45 Grams (21.95 moles) of de-ionized (DI) water followed by 195.22 grams (1.0 mole) of N-methylglucamine were placed into a two-liter, four-necked, round-bottomed glass flask fitted with a stirrer having a vapor-tight seal, an addition funnel with a pressure equalizing arm, a water-cooled condenser, and a thermometer. Stirring is begun at the start of the introduction of the N-methylglucamine. The stirring rate was between 100 to 120 rpm. The fluffy white powder of N-methylglucamine was soluble in water and most (about 98%) dissolved within about ten (10) minutes at ambient temperature. Not all the solid needs to be dissolved to begin the oxidation with hydrogen peroxide. The water introduced with the aqueous solution of hydrogen peroxide provided the needed additional solvent to bring all the N-methylglucamine into solution.

The dropwise addition of 113.39 grams of 30% aqueous hydrogen peroxide solution (34.015 grams, 1.0 mole of pure hydrogen peroxide) began at a rate of 2.4 ml/min (density of 30% aqueous $H_{20}O_2$ is 1.110 g.ml) at ambient temperature and continued for thirty (30) minutes. After thirty minutes, seventy (70) percent (71.5 ml) of the total aqueous hydrogen peroxide were introduced. The hydrogen peroxide addition was stopped and the reaction was allowed to catch up to the quantity of hydrogen peroxide charged. The temperature slowly rose. As the temperature rose, the rate of oxidation increased so that in about twenty-five to twenty-eight minutes the reaction mixture reached a temperature of 45 to 47° C. At this point, cooling of the reactor began by placing a cold water bath around the flask to keep the reaction rate from accelerating beyond a temperature of 55° C. A bath of two liters of 5–8° C. water accomplished this control over the reaction, allowing the temperature to peak at 55° C. at about 1.1 hours (65 minutes) from the start of the addition of hydrogen peroxide. Over the next five minutes, the temperature began to recede. When the reaction mixture reached 53° C. the addition of hydrogen peroxide began at a rate of 1.54 ml/min with full external cooling of the reaction flask. At this rate of addition, all the remaining hydrogen peroxide solution were introduced in twenty (20) minutes. The temperature during this time period remained almost constant at about 50° C. with cooling by the cold-water bath.

The cooling was accomplished with the cold-water bath by allowing the cooling bath temperature to rise form the initial 8° C. to 25° C. at which temperature the tepid water was replaced with another two liters of 8° C. water. The heat capacity of the water over this 17° C. temperature rise was sufficient to remove the heat from this exothermic oxidation.

When the reaction temperature receded to about 40° C. with all the hydrogen peroxide having been introduced, the cooling bath was removed and the colorless to very light tan aqueous solution was allowed to stir for another thirty (30) minutes. The total reaction time was approximately two and three quarter (2.75) hours.

The aqueous solution should be 704.1 grams in weight with a volume of about 652 mls at a weight fraction of 0.30 gram N-hydroxy-N-methylglucamine per gram of solution. The solution was stored in a dark bottle under refrigeration until used for controlling aqueous phase polymer growth in a suspension polymerization.

EXAMPLE 2

Nitrosation of N-Methylglucamine To Give a 30% Aqueous Solution of N-Nitroso-N-Methylglucamine This reaction was also exothermic and the temperature was kept below 50° C. In order that the molecule does not begin to decompose.

434.13 Grams (24.10 moles) of de-ionized (DI) water followed by 195.22 grams (1.0 mole) of N-methylglucamine were placed into the reactor described above in Example 1. The stirring rate was set at 100 to 120 rpm. When essentially all (about 98%) of the N-methylglucamine has dissolved, 69.0 grams of anhydrous sodium nitrite (1.0 mole, NaNO2) was introduced at a rate such that the sodium nitrite does not form clumps. An addition time of about five (5) minutes was sufficient to avoid clumping. At this point, the reaction mixture was not a true solution and appeared milky white.

The nitrosation reaction was carried out over about two hours (2.0 hours). Commercial concentrated sulfuric acid, 50.0 grams of 95 to 98% assay (0.5 mole, density=1.84 g/ml) is begun to be added at a rate of 1.0 ml/min. At this rate, the sulfuric acid was introduced over a period of fifty (50) minutes. The reaction exotherm carried the temperature upward and, at 40° C., external cooling was applied via a cold-water bath so as to keep the peak temperature below 50° C. After all the sulfuric acid had been introduced, the turbid mixture was stirred for another seventy (70) minutes (1.167 hours), during which time the cooling bath was removed after the temperature has peaked and had begun to recede.

The opaque white liquid was packaged in a dark bottle and placed in a refrigerator for storage until used in a suspension polymerization. The yield of liquid slurry was about 748 grams with a weight fraction of 0.30 of N-nitroso-N-methylglucamine.

Obviously, numerous modification and variations of the present invention are possible in light of the above teachings. It is therefore to be understood that within the scope of the appended claims the invention may be practiced otherwise than as specifically described therein.

What is claimed is:

1. An inhibitor comprising a free radical quenching agent having a hydrophilic tail wherein said inhibitor quenches free radical polymerization in an aqueous phase and remains substantially in the aqueous phase throughout the polymerization.

2. The inhibitor of claim 1 wherein said free radical quenching agent is a N-hydroxylamine.

3. The inhibitor of claim 2 wherein said hydrophilic tail is a polyhydric alcohol tail.

4. The inhibitor of claim 3 wherein said polyhydric alcohol tail comprises from about three carbon atoms to about one thousand carbon atoms, each of said carbon atoms being attached to a hydroxyl group except the carbon atom attached to the nitrogen of said N-hydroxylamine.

5. The inhibitor of claim 1 wherein said free radical quenching agent is N-nitrosoamine.

6. The inhibitor of claim 5 wherein said hydrophilic tail is a polyhydric alcohol tail.

7. The inhibitor of claim 6 wherein said polyhydric alcohol tail comprises from about three carbon atoms to about one thousand carbon atoms, each of said carbon atoms being attached to a hydroxyl group except the carbon atom attached to the nitrogen of a N-nitrosoamine.

8. The inhibitor of claim 1 wherein said hydrophilic tail consists essentially of sugar molecules, dextrans, inositol, sorbitol, polyvinylalcohols, polyethylene oxides, amino acids, oligomers of N-vinylpyrrolidinone, oligomers of N-vinylformamide, oligomers of acrylamide, oligomers of methacrylamide, p-benzamide or p-benzenesulfonamide.

9. The inhibitor of claim 1 wherein said free radical quenching agent is N-hydroxyl-methylglucamine.

10. The inhibitor of claim 1 wherein said free radical quenching agent is N-nitroso-N-methylglucamine.

11. The inhibitor of claim 1 wherein said inhibitor is a concentrate in a liquid medium.

12. The inhibitor of claim 11 wherein said liquid medium consists essentially of water, alcohol and mixtures thereof.

13. The inhibitor of claim 11 wherein said free radical quenching agent is N-hydroxyl-N-methylglucamine and said liquid medium comprises water.

14. The inhibitor of claim 13 wherein said N-hydroxyl-N-methylglucamine is from about 15 to about 40% of said liquid medium.

15. The inhibitor of claim 11 wherein said free radical quenching agent is N-nitroso-N-methylglucamine and said liquid medium comprises water.

16. The inhibitor of claim 15 wherein said N-nitroso-N-methylglucamine is from about 15 to about 40% of said liquid medium.

* * * * *